United States Patent [19]

Drewlow

[11] Patent Number: Plant 6,309

[45] Date of Patent: Sep. 27, 1988

[54] IMPATIENS PLANT NAMED MIRACH

[75] Inventor: Lyndon W. Drewlow, Ashtabula, Ohio

[73] Assignee: Mikkelsens, Inc., Ashtabula, Ohio

[21] Appl. No.: 916,568

[22] Filed: Oct. 8, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

An Impatiens plant named Mirach, having intense bright red flower color which does not fade under high light and high temperature conditions; compact and self-branching growth habit; two flowers carried on most leaf axils, producing a floriferous habit, and having green leaves variegated with cream along the midrib.

1 Drawing Sheet

1

The present invention relates to a new and distinctive cultivar of Impatiens plant, botanically known as Impatiens, and referred to by the cultivar name Mirach. Mirach was developed by me through controlled breeding by crossing Mikkelsen Seedling No. 84-1227-5 (seed parent) with Mikkelsen Seedling No. 84-1229-4 (pollen parent). Asexual reproduction of the progeny of the stated cross by terminal or stem cuttings performed by me in Ashtabula, Ohio has shown that unique features of this new impatiens are stabilized and are reproduced true to type in successive propagations.

The following characteristics distinguish the new impatiens from both its parent varieties and other cultivated impatiens of this type known and used in the floriculture industry. In certain instances the characteristics are compared with similar characteristics of other cultivars. Of the cultivars referred to, Flare is disclosed in U.S. Plant Pat. No. 5,135; Solared is disclosed in U.S. Plant Pat. No. 5,131; Red Plant is disclosed in U.S. Plant Pat. No. 4,690, and Zenith and Nova are disclosed in pending applications.

1. Mirach is deeper red in color than Red Planet, Flare, and Solared. Under high temperatures and bright sun the flower color does not fade and burn like Flare and Red Plant.

2. The flowers are larger in size than the flowers of Flare, Solared and Red Planet, but not quite as large as the flowers of Zenith.

3. The leaf variegation color and pattern of Mirach is similar to Zenith; it is not as heavily variegated as Red Planet, and similar in amount of variegation to Flare, Solared and Nova.

4. Mirach is larger and more vigorous than Solared but not as mounted in form. Mirach is similar in size and growth habit to Nova and Zenith, and more compact and dense than Flare and Red Plant.

5. Most but not all leaf axils of Mirach have two flowers, while Nova and Solared have two flowers at each leaf axil. Red Planet, Flare and Zenith have only one flower at each leaf axil.

6. Green leaf color of Mirach is similar to Red Planet, Flare and Solared. Zenith is a brighter green and Nova a darker green. Underside of leaves are yellow green which is similar to Red Planet, Flare, Solared and Zenith, with Nova having a purplish underside.

7. Mirach is more branched than either Red Planet or Flare, making it suitable for 4" pots, hanging baskets and bedding plant use.

2

8. Mirach is 7 to 10 days earlier in flowering to Red Planet, Flare and Solared, and similar in flowering time to Nova and Zenith.

9. The leaf size of Mirach is larger than Solared, similar to Red Planet, Flare and Zenith, and slightly smaller than Nova.

10. Mirach has demonstrated the ability to continue to flower without fading of the flower or loss of leaves under the low light and high temperature environment of a home.

The accompanying colored photograph is a top perspective view of Mirach, showing colors as true as it is reasonably possible to obtain in a colored reproduction of this type.

The following is a detailed description of my impatiens cultivar based on plants produced under commercial practices in Ashtabula, Ohio under both greenhouse and outdoor conditions. The photograph was taken of a greenhouse-grown plant in early June. Color references are made to the Royal Horticultural Society Colour Chart except where general terms of ordinary dictionary significance are used.

Parentage:

A controlled cross between Mikkelsen Seedling No. 84-1227-5 and Mikkelsen Seedling No. 84-1229-4.

Propagation:

(A) *Type cutting.*—Stem 15 mm long will develop to 4 to 5 cm long in 18 to 21 days.

(B) *Time to root.*—8 to 10 days at 23° C. summer, and 10 to 12 days at 20° C. winter.

(C) *Rooting habit.*—Heavy, fibrous.

Plant description:

(A) *Form.*—Compact, self-branching, red stemmed, symmetrically mounted, vigorous growing herb.

(B) *Habit of growth.*—Vigorous, self-branching, compact, semi-mounted, continuous flowering.

(C) *Foliage description.*—Broad dark green leaves with cream variegation, with a toothed pattern at the major veins extending three-fourths of the way up mature leaves. (1) Size: Mature leaves are 9 to 10 cm long and 2.5 to 3.0 cm wide. (2)Shape: Lanceolate with acuminate apex and glabrous underside. (3) Texture: Rugose upper side, glabrous underside. (4) Margin: Finely serrated, with fine cilia. (5) Color: Young foliage top side 146A, variegated with 153D. Under side: 146C, variegated with 12D. Mature foliage top side 147A, variegated with 153D. Under side: 147C, variegated with 23C. (6) Venation: Pinnate, midrib is pinkish red.

Flowering description:

(A) *Flowering habits.*—Flowers continuously from leaf whorl in progressively orderly manner, taking 5 to 7 days from large bud to bloom. Most leaf axils have two flower buds, and the secondary buds do not open until all primary flowers in an axil have opened. Before the secondary flowers finish opening, the primary flowers on the whorl above start to open. Flowers last 2 to 3 weeks.

(B) *Natural flowering season.*—Indeterminant and continuous. Quantity of flowering increases with increasing levels of light.

(C) *Flower buds.*—Ellipsoidal, flowers perfect, deep red spur 3.0 cm long on mature buds, with throat behind ovary and originating from the major sepal.

(D) *Flowers borne.*—On individual short 3.5 to 4.0 cm reddish pedicels at maturity from a whorl of 5 to 6 leaves; flowering progressively around the whorl with all primary flowers in a whorl opening before the secondary ones start to open.

(E) *Quantity of flowers.*—Very floriferous due to most leaf axils having two flower buds per leaf. Flowering development is continuous so that tight buds and mature flowers are present at the same time.

(F) *Petals.*—(1) Shape: Heart shaped with all petals quite similar in size. (2) Color: Top side in summer when opening, 42A; under side 44A. Color does not fade. (3) Number of petals: Five (5) in number. (4) Size of flowers: 5.0 to 5.5 cm in diameter.

(G) *Reproductive organs.*—(1) Stamens: Five (5) in number. (a) Anther shape: Hooded, color cream with reddish tint. (b) Pollen color: Cream. (2) Pistels (a) Stigma: Five (5) in number, segmented column shaped, color cream. (b) Style color: Cream. (c) Ovaries: Five (5) in number, celled, size 5 mm until fertilized, color green.

Disease resistance: No significant disease problem noted to date.

I claim:

1. A new and distinct Impatiens plant named Mirach, as described and illustrated, and particularly characterized by its intense bright red flower color which does not fade under high light and high temperature conditions; compact and self-branching growth habit; two flowers carried on most leaf axils, producing a floriferous habit, and by its green leaves variegated with cream along the midrib.

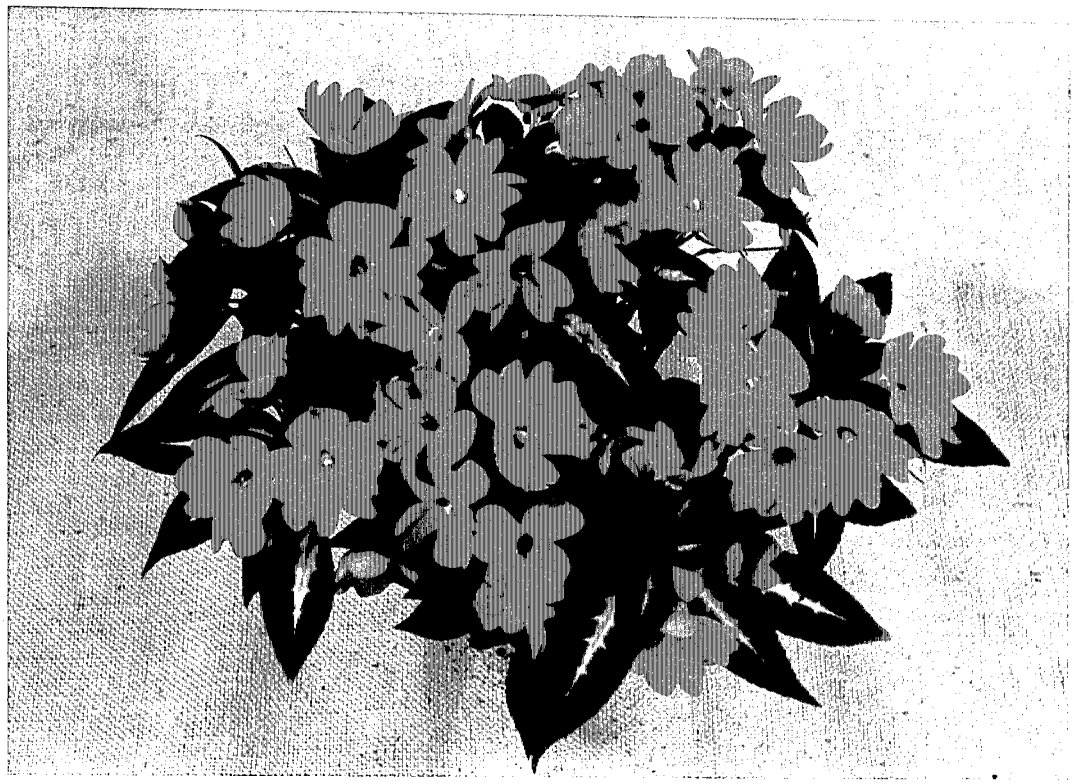

* * * * *